United States Patent [19]

Rasheed et al.

[11] 4,139,362
[45] Feb. 13, 1979

[54] BIOCIDALLY-ACTIVE 1,2,3-BENZOTRISULFIDES

[75] Inventors: Khalid Rasheed, Weslaco; James D. Warkentin, McAllen, both of Tex.

[73] Assignee: The Ansul Company, Marinette, Wis.

[21] Appl. No.: 821,978

[22] Filed: Aug. 4, 1977

Related U.S. Application Data

[63] Continuation-in-part of Ser. No. 618,255, Sep. 30, 1975, Pat. No. 4,084,954.

[51] Int. Cl.$^2$ .................... A61K 31/385; A01N 9/12; A01N 9/14; C07D 341/00
[52] U.S. Cl. ........................................ 71/90; 424/277; 260/327 H; 260/455 A
[58] Field of Search ................. 260/327 H; 424/277; 71/90

[56] References Cited

U.S. PATENT DOCUMENTS

| | | | |
|---|---|---|---|
| 3,491,119 | 1/1970 | Fields | 260/327 H |
| 4,084,954 | 4/1978 | Rasheed et al. | 260/327 H |

OTHER PUBLICATIONS

Breslow et al, Multi-Sulfur and Sulfur and Oxygen 5- and 6-Membered Heterocycles, Part 1, Chapter 3, pp. 68-69, Interscience Publishers, NY, (1966).
Guha et al, Chem. Abstracts, vol. 20, p. 1797, (1926).
Steinle et al, Chem. Abstracts, vol. 76, abst. 140,653j, (1972).
Steinle et al, Chem. Abstracts, vol. 80, abst. No. 108,458w, (1974).
Feher, et al., C. A. 70:16155q, (1973).

*Primary Examiner*—John D. Randolph
*Attorney, Agent, or Firm*—Morgan, Finnegan, Pine, Foley & Lee

[57] ABSTRACT 1,2,3-Benzotrisulfide compounds are disclosed including the novel method of preparing said compounds and their biocidal activity.

30 Claims, No Drawings

BIOCIDALLY-ACTIVE 1,2,3-BENZOTRISULFIDES

CROSS-REFERENCE TO RELATED APPLICATIONS

This application is a continuation-in-part of Ser. No. 618,255, filed Sept. 30, 1975, now U.S. Pat. No. 4,084,954, granted Apr. 18, 1978.

BACKGROUND OF THE INVENTION

This invention relates generally to new and useful biocidally active compounds. More specifically, it relates to novel 1,2,3-benzotrisulfide compounds prepared by an unusual but highly simple reaction. In fact, it is due to this synthesis that the numerous derivatives disclosed herein can be obtained so easily and in good yields.

The novel compounds of this invention are useful in treating pests associated with growing plants in order to beneficially enchance the growth and/or yield-potential of said growing plants. This is accomplished by applying a biocidally active amount of the subject compound to soil, seed or the growing plant. The term "pests" as used herein is meant to include plant pests such as weeds and fungi, and animal pests such as arachnids, nematodes, or insects.

The concentration, rate and physical form of the administered compound are determined by the particular application, said application comprising one or more of the following:

(1) herbicidal
(2) fungicidal
(3) acaricidal
(4) nematocidal
(5) insecticidal

Generally, for each particular application, there will be a preferred range with respect to concentration, a preferred amount with respect to rate and a preferred type with respect to formulation.

For purposes of this disclosure and for the sake of convenience and clarity, certain terms used herein are defined as follows:

The phrase "treating pests associated with growing plants" signifies the application of a compound as herein defined to pests associated with growing plants which embraces germinating plants, e.g. seeds, sprouts, seedlings, and fully grown plants. The mode of application will depend on the desired end use. For example, if the treatment is for pre-emergent herbicidal use, the compound will be administered into the soil which contains the growing seeds. In contrast, when used as a post-emergent herbicide, the compound will be applied to the growing plants after seeds have germinated.

When treatment comprises foliar fungicidal application, the compound is administered, as a spray, directly onto th leaves and other above ground portions of diseased plants.

For use as an acaricide, the compound may be applied by contacting the leaves (or plant) directly or as a soil incorporation in the soil where the plant is growing.

For use as a soil or seed treatment fungicide, the compound is usually applied as a seed treatment, or as a drench and/or incorporation to the soil containing the seed or the growing plant.

For use as a nematocide, the compound is normally applied directly as a drench and/or incorporation to the soil containing the growing plant.

For use as an insecticide, the compound is usually applied topically to the above ground portions of infested plants and/or to the soil containing the growing plants.

All of the aforesaid treatments, whatever the objective, have a unitary result. That is, they beneficially enhance or improve the growth and/or yield potential of the treated plant.

The term "biocidally active amount" means an amount of compound which effectively permits the desired objective.

SUMMARY OF THE INVENTION

Accordingly, this invention is concerned with compounds of the formulae:

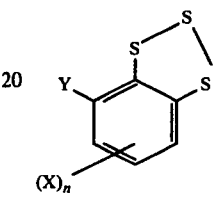

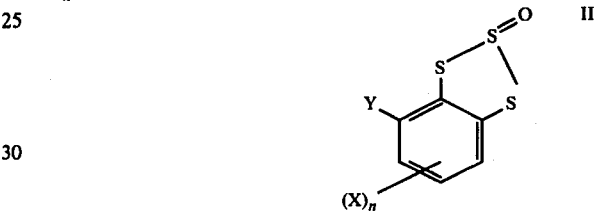

wherein Y is selected from hydrogen, cyano, alkylsulfonyl, nitro and trifluoromethyl; X is selected from alkyl and alkenyl of up to 6 carbon atoms, nitro, trichloromethyl, trifluoromethyl, trifluoromethoxy, trifluoromethylthio, trifluoromethylsulfoxyl, trifluoromethylsulfonyl, methoxymethyl, cyano, carboxy, carbamyl, halogen (F, Cl, Br, I), hydroxy, acetylamino, amino, N-phenylamino, N,N-diallylamino, alkoxy, N-morpholino, N-piperidino, N-piperazino, N-pyrrolidino, dimethylaminodithiocarbamyl, carboalkoxy, alkylthio, mono- and dialkylamino, N-alkylcarbamyl, N,N-dialkylcarbamyl, alkylsulfoxy, alkylsulfonyl, said alkyl groups containing from 1 to 4 carbon atoms; n is an integer from 0 to 3; and salts thereof.

Of particular interest are compounds as shown above having formula I wherein Y is nitro and n is zero, which is 4-nitro-1,2,3-benzotrisulfide.

Other preferred compounds include those as shown above having formula I wherein Y is nitro and n is 1 such as:

4-nitro-6-trifluoromethyl-1,2,3-benzotrisulfide
4-nitro-6-chloro-1,2,3-benzotrisulfide.

Still others which are preferred as those as shown above having formula I wherein Y is trifluoromethyl and n is 2 such as:

4-dimethylamino-5-nitro-6-trifluoromethyl-1,2,3-benzotrisulfide.

Another compound which is preferred as shown above having formula II wherein Y is nitro and n is 1 is:
4-nitro-6-trifluoromethyl-1,2,3-benzotrisulfoxide (2).

Also within the purview of this invention is the novel process for preparing such compounds as well as the use of such compounds to beneficially enhance the growth and/or yield-potential of plants.

DETAILED DESCRIPTION OF THE INVENTION

The compounds of this invention are prepared by a novel procedure. It is this synthetic method which allows for the formation of the numerous compounds disclosed herein. Compounds which would ordinarily be inaccessible or at best, tedious and difficult to make, are rendered available by an unusually simple and mild synthesis.

The process can be expressed by the following reactions:

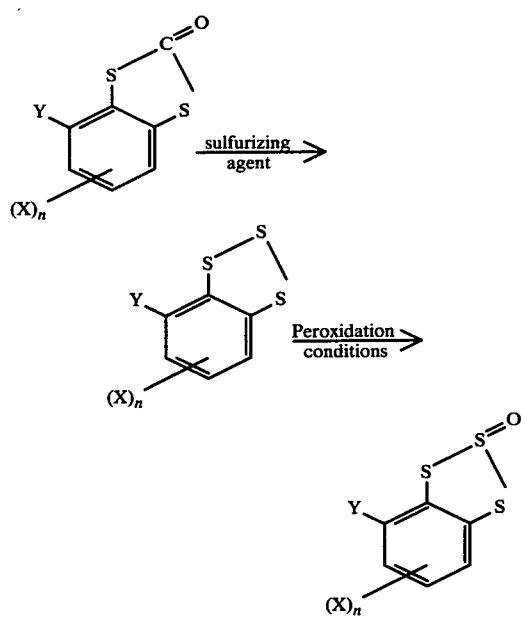

wherein Y is selected from hydrogen, cyano, alkylsulfonyl, nitro and trifluoromethyl; X is selected from alkyl and alkenyl of up to 6 carbon atoms, nitro, trichloromethyl, trifluoromethyl, trifluoromethoxy, trifluoromethylthio, trifluoromethylsulfoxyl, trifluoromethylsulfonyl, methoxymethyl, cyano, carboxy, carbamyl, halogen (F, Cl, Br, I), hydroxy, acetylamino, amino, N-phenylamino, N,N-diallylamino, alkoxy, N-morpholino, N-piperidino, N-piperazino, N-pyrrolidino, dimethylaminodithiocarbamyl, carboalkoxy, alkylthio, mono- and dialkylamino, N-alkylcarbamyl, N,N-dialkylcarbamyl, alkylsulfoxy, alkylsulfonyl, said alkyl groups containing from 1 to 4 carbon atoms and n is an integer from 0 to 3.

Starting material D is a 1,3-benzodithiole-2-one compound whose synthesis is described in detail in copending parent application Ser. No. 618,255, filed Sept. 30, 1975, now U.S. Pat. No. 4,084,954. Generally, the synthesis involves reacting an α-halonitrobenzene derivative with an N,N-dialkyldithiocarbamic acid salt as follows:

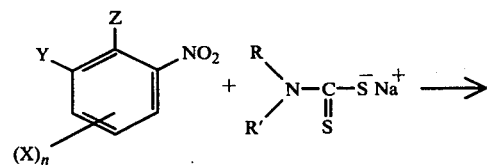

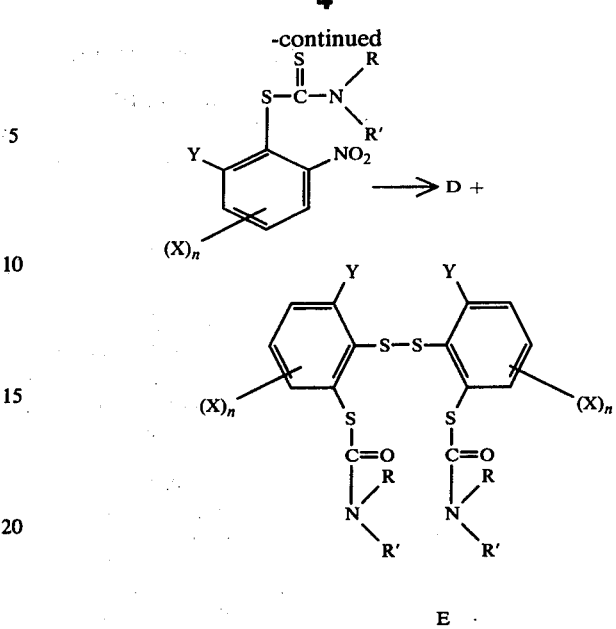

wherein Z is halogen (F, Cl, Br, I) or alkoxy; R and R' are each alkyl groups, straight- or branch-chained, containing from 1 to 4 carbon atoms; and Y, X and n are as defined above.

Co-product E which forms, in some instances, when compound D is prepared can be isolated. It will also undergo conversion to compound I under the same conditions for preparing I from compound D, i.e. under sulfurizing conditions.

The conversion of compound D to product I is effected under sulfurizing conditions using a sulfurizing agent which is known to convert carbonyl to thiocarbonyl ($>C=O \rightarrow >C=S$). One such sulfurizing agent is sodium hydrosulfide. Other employable agents are disodium trithiocarbonate, potassium thiocyanate, etc.

The attractiveness of the above process is that under relatively mild conditions, and in a single step, one can obtain the desired compounds in good yields.

The novelty of this synthetic method is clearly evident to one skilled in the art. It enables one to create one ring configuration from another, quite unexpectedly.

The reaction process is carried out in the temperature range of from 0° C. to 200° C. In many instances, the reaction proceeds at room temperature or lower, whereas, in some cases, elevated temperatures may be desired in order to accelerate the reaction.

The reaction is usually carried out in a solvent, although the solvent may be omitted if effective dissolution of materials is possible. A solvent is generally preferred, however, and it can be any solvent which does not enter into the reaction and in which the reactants are soluble to some extent. Suitable solvents are dimethylformamide, dimethylsulfoxide, acetone and methyl isobutyl ketone.

The mole ratio of reagents is normally 1 to 1, however, it is generally preferred to use a large excess of sulfurizing agent to ensure more complete reaction.

The work-up is standard — product is obtained by precipitation, washing, drying and recrystallization if necessary.

The 1,2,3-benzotrisulfoxide (2) compounds disclosed herein are obtained by conversion of the corresponding 1,2,3-benzotrisulfide compounds. The conversion of >S to >S=O is well known in the chemical literature and, is generally effected by treatment under peroxidation conditions, e.g., by using a peracid such as peracetic acid. The term peroxidation in this context means any peroxide material capable of converting sulfur to sulfoxide.

The biocidal processes of this invention comprise applying a biocidally effective amount of a compound disclosed herein to soil, seed or growing plant. The compounds are formulated for use either as sprays made up by adding water to emulsifiable concentrates or wettable powders, as granules or as dispersions on carriers such as attapulgite clay granules, peat moss, fertilizer, vermiculite, etc. The compounds are quite insoluble in water, and hence, for the preparation of emulsions or wettable powders, the compounds are preferably formulated with wetting agents.

Since numerous compounds disclosed herein are free bases and acids, they can be converted to acid salts (free bases) and base salts (free acids).

The acid-addition and base-addition salts are within the purview of this invention. The acid-addition salts are easily prepared by treating the amine base with a substantially equimolar amount of a chosen acid in an aqueous solution or in a suitable organic solvent such as methanol or ethanol. The only restriction on the acid used is that it provides acceptable ions, i.e., those which do not deleteriously affect the growing plants. The base-addition salts are prepared in a similar manner except that base instead of acid is added. The same restriction with respect to acceptable ions applies.

For herbicidal use, the compounds disclosed herein are applied at a rate of from 0.5 lbs a.i./acre to 8.0 lbs a.i./acre.

For soil fungicidal use, the compounds disclosed herein are applied at a rate of from 0.25 to 40.0 lbs a.i./acre.

For seed treatment fungicidal use the compounds disclosed herein are applied at a rate of from 2.0 to 10.0 ounces per 100 lbs of crop seed.

For foliar fungicidal use, the compounds disclosed herein are applied at a rate of about 200 parts per million in a suitable solvent, such as water.

For acaricidal use, the compounds disclosed herein are applied at a rate of from 30 to 1000 parts per million in a suitable solvent, such as water.

For nematocidal use, the compounds disclosed herein are applied at a rate of from 15 to 20 parts per million in a suitable solvent, such as water.

For insecticidal use, the compounds disclosed herein are applied at a rate of from 0.2% to 10.0% in a suitable solvent, such as water.

EXAMPLE I

4-Nitro-6-trifluoromethyl-1,2,3-benzotrisulfide

A. To a stirred and tap-water cooled solution of 2.81 g (10 mmole) of 4-nitro-6-trifluoromethyl-1,3-benzodithiole-2-one was added 4.45 g (50 mmole) of NaHS as a powder. The mixture was allowed to stir overnight, poured into 100 ml of water which after acidification with conc. HCl was extracted with methylene chloride. The organic extract was washed with three 100 ml portions of water, dried ($Na_2SO_4$) and filtered. The filtrate was evaporated in vac. and the solid residue recrystallized from ethanol. Obtained 2.2 g (77%) of 4-nitro-6-trifluoromethyl-1,2,3-benzotrisulfide as red crystals, m.p. 108–110° C.

Anal. Calcd. for $C_7H_2F_3NO_2S_3$: C, 29.47; H, 0.70; N, 4.91. Found: C, 29.58; H, 0.85; N, 5.24. Mol. wt. (mass spect.) 285. NMR ($CDCl_3$): 8.43δ (m, 1H); 8.03 (m, 1H).

B. To a stirred and cooled solution of 4-nitro-6-trifluoromethyl-1,3-benzodithiole-2-one (14.05 g, 0.05 M) in DMSO (150 ml) was added dropwise a solution of disodium trithiocarbonate (48.15 g, 0.12 M of 40% aqueous solution). The reaction mixture was permitted to stir for 60 minutes at about 15° C. and thereafter for 2½ hours at ambient temperatures.

The resulting solution was poured into an excess of water, acidified and extracted and chloroform (3 × 100 ml). The organic layer was separated, dried, stripped free of solvent and chromatographed over silica gel. Elution with hexane removes elemental sulfur. Another elution with hexane yields the desired product.

EXAMPLE II

The procedure of Example I is repeated wherein the following substituted 1,3-benzodithiole-2-one derivatives are used in place of 4-nitro-6-trifluoromethyl-1,3-benzodithiole-2-one to provide the corresponding products:

| Substituted 1,3-benzodithiole-2-one derivative | Product |
| --- | --- |
| 6-methyl-4-nitro-1,3-benzodithiole-2-one | 6-methyl-4-nitro-1,2,3-benzotrisulfide |
| 4,6-dinitro-1,3-benzodithiole-2-one | 4,6-dinitro-1,2,3-benzotrisulfide |
| 6-fluoro-4-nitro-1,3-benzodithiole-2-one | 6-fluoro-4-nitro-1,2,3-benzotrisulfide |
| 6-chloro-4-nitro-1,3-benzodithiole-2-one | 6-chloro-4-nitro-1,2,3-benzotrisulfide |
| 6-chloro-7-methyl-4-nitro-1,3-benzodithiole-2-one | 6-chloro-7-methyl-4-nitro-1,2,3-benzotrisulfide |
| 7-dimethylaminodithiocarbamyl-4-nitro-6-trifluoromethyl-1,3-benzodithiole-2-one | 7-dimethylaminodithiocarbamyl-4-nitro-6-trifluoromethyl-1,2,3-benzotrisulfide |
| 7-chloro-4-nitro-6-trifluoromethyl-1,3-benzodithiole-2-one | 7-chloro-4-nitro-6-trifluoromethyl-1,2,3-benzotrisulfide |
| 4-nitro-1,3-benzodithiole-2-one | 4-nitro-1,2,3-benzotrisulfide |
| 5,7-dimethyl-4,6-dinitro-1,3-benzodithiole-2-one | 5,7-dimethyl-4,6-dinitro-1,2 3-benzotrisulfide |
| 7-dimethylamino-6-nitro-4-trifluoromethyl-1,3-benzodithiole-2-one | 7-dimethylamino-6-nitro-4-trifluoromethyl-1,2,3-benzotrisulfide |
| 7-di-n-propylamino-6-nitro-4-trifluoromethyl-1,3-benzodithiole-2-one | 7-di-n-propylamino-6-nitro-4-trifluoromethyl-1,2,3-benzotrisulfide |
| 7-monoisopropylamino-6-nitro-4-trifluoromethyl-1,3-benzodithiole-2-one | 7-monoisopropylamino-6-nitro-4-trifluoromethyl-1,2,3-benzotrisulfide |
| 7-monopropylamino-6-nitro-4-trifluoromethyl-1,3-benzodithiole-2-one | 7-monopropylamino-6-nitro-4-trifluoromethyl-1,2,3-benzotrisulfide |
| 7-diethylamino-6-nitro-4-trifluoromethyl-1,3-benzodithiole-2-one | 7-diethylamino-6-nitro-4-trifluoromethyl-1,2,3-benzotrisulfide |
| 6-nitro-7-n-propylthio-4-trifluoromethyl-1,3-benzodithiole-2-one | 6-nitro-7-n-propylthio-4-trifluoromethyl-1,2,3-benzotrisulfide |
| 7-isopropylthio-6-nitro-4-trifluoromethyl-1,3-benzodithiole-2-one | 7-isopropylthio-6-nitro-4-trifluoromethyl-1,2,3-benzotrisulfide |
| 6-cyano-4-nitro-1,3-benzodithiole-2-one | 6-cyano-4-nitro-1,2,3-benzotrisulfide |
| 7-diallylamino-6-nitro-4-trifluoromethyl-1,3-benzodithiole-2-one | 7-diallylamino-6-nitro-4-trifluoromethyl-1,2,3-benzotrisulfide |
| 7-methylamino-6-nitro-4-trifluoromethyl-1,3-benzodithiole-2-one | 7-methylamino-6-nitro-4-trifluoromethyl-1,2,3-benzotrisulfide |
| 7-mono-n-butylamino-6-nitro-4-trifluoromethyl-1,3-benzodithiole-2-one | 7-mono-n-butylamino-6-nitro-4-trifluoromethyl-1,2,3-benzotrisulfide |
| 7-di-n-butylamino-6-nitro-4-trifluoromethyl-1,3-benzodithiole-2-one | 7-di-n-butylamino-6-nitro-4-trifluoromethyl-1,2,3-benzotrisulfide |
| 7-monophenylamino-6-nitro-4-trifluoromethyl-1,3-benzodithiole-2-one | 7-monophenylamino-6-nitro-4-trifluoromethyl-1,2,3-benzotrisulfide |

| Substituted 1,3-benzodithiole-2-one derivative | Product |
|---|---|
| 6-nitro-7-piperidino-4-trifluoromethyl-1,3-benzo-dithiole-2-one | 6-nitro-7-piperidino-4-trifluoromethyl-1,2,3-benzotrisulfide |
| 7-morpholino-6-nitro-4-trifluoromethyl-1,3-benzo-dithiole-2-one | 7-morpholino-6-nitro-4-trifluoromethyl-1,2,3-benzotrisulfide |
| 6-nitro-7-pyrrolidino-4-trifluoromethyl-1,3-benzodi-thiole-2-one | 6-nitro-7-pyrrolidino-4-trifluoromethyl-1,2,3-benzotrisulfide |
| 5-nitro-1,3-benzodithiole-2-one | 5-nitro-1,2,3-benzotrisulfide |
| 5-trifluoromethyl-1,3-benzo-dithiole-2-one | 5-trifluoromethyl-1,2,3-benzotrisulfide |

EXAMPLE III

The procedure of Example I is repeated wherein the following 1,3-benzodithiole-2-one derivatives are used in place of 4-nitro-6-trifluoromethyl-1,3-benzodithiole-2-one to provide corresponding products:

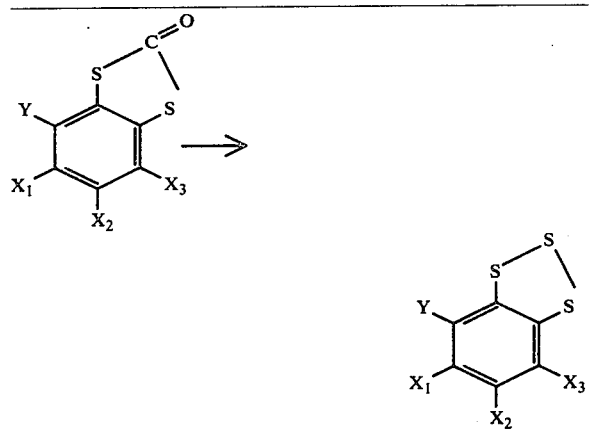

| | halobenzene derivative | | |
|---|---|---|---|
| Y | $X_1$ | $X_2$ | $X_3$ |
| $NO_2$ | allyl | H | H |
| $NO_2$ | hexyl | H | H |
| $NO_2$ | H | $CCl_3$ | H |
| $NO_2$ | H | $CF_3O$ | H |
| $CF_3$ | H | $CH_3SO_2$ | H |
| $NO_2$ | H | $CF_3S$ | H |
| $NO_2$ | H | $CF_3SO$ | H |
| $NO_2$ | H | CN | H |
| $NO_2$ | H | $CF_3SO_2$ | H |
| $NO_2$ | H | H | H |
| $NO_2$ | H | $CH_3OCH_2$ | H |
| $CF_3$ | H | CN | H |
| $CF_3$ | H | COOH | H |
| $CF_3$ | H | OH | H |
| $CF_3$ | H | $NH_2$ | H |

EXAMPLE IV

4-Nitro-6-trifluoromethyl-1,2,3-benzotrisulfoxide (2)

To a stirred slurry of 1.19 g (4.1 mmole) of 4-nitro-6-trifluoromethyl-1,2,3-benzotrisulfide in 10 ml of glacial acetic acid at ∼ 35° C. was added dropwise 3.04 g (16 mmole) of 40% per acetic acid within 2–3 minutes. There occurred an exothermic reaction accompanied by dissolution of the solid (tap-water cooling). Mixture allowed to stir for 15 minutes, poured into 150 ml of cold water and the aqueous mixture extracted with two 50 ml portions of methylene chloride. The organic extract was washed with two 400 ml portions of water, dried ($Na_2SO_4$) and after filtration the solvent was removed in vac. The residual solid was recrystallized from ethanol. Obtained 0.4 g (33%) of 4-nitro-6-trifluoromethyl-1,2,3-benzotrisulfoxide (2), m.p. 142–143° C.

Anal. calcd. for $C_7H_2F_3NO_3S_3$: C, 27.90; H, 0.66; N, 4.65. Found: C, 28.05; H, 0.78; N, 4.37.

EXAMPLE V

For determination of herbicidal activity for the herein disclosed compounds, the following screen was used: The candidate compound is applied at 8 lb/A in 40 gal/A to one foot square flats containing seeds or plants of the test plant species. Visual ratings of phytotoxicity are made after 7 and 14 days. The phytotoxicity rating system is based on 0 = no control and 10 = complete kill or 100% control.

For post-emergent use, the flats are planted with the desired plant species 7–9 days prior to spraying. By spraying time a well established flat of plants is ready for spraying. For incorporated pre-emergence use, the flats are prepared and planted with seed of the various species. A sheet of plastic is then placed over the seed and a measured quantity of screened soil normally used for covering the seed is placed on top. The flat is then ready for spraying. After spraying, the soil on top of the sheet of plastic is mixed thoroughly and spread evenly over the surface of the flat.

The plant species used in herbicide screening are corn (*Zea mays* L.), wheat (*Triticum avesticum* L.), cotton (*Gossypium hirsutum* L.), soybeans (Glycine max L.), barnyard-grass (*Echinochloa crusgalli* L. Beauv), foxtail (*Setaria viridis* L. Beauv), morningglory (*Ipomea purpurea* L. Roth), and pigweed (*Amaranthus retroflexus* L.).

EXAMPLE VI

For determination of soil fungicidal activity for the herein disclosed compounds, the following screen was used: Two potato-dextrose-agar plates of the desired fungal organism are blended in a Waring blender with 50 mls of sterile water. The resulting mixture is added to 3000 g of sterile soil in a plastic bag and thoroughly blended. Cucumber seeds are planted in 4 oz. cups containing a measured amount of the inoculated soil mixture. Finally, 10 mls of the candidate compound at 40 lb/A is atomized as a drench over the prepared soil. After 14 days evaluations are made based on the number of surviving seedlings in the treated cup compared to the untreated check.

The organisms used in the primary soil fungicide screen are *Rhizoctonia solani* and *Pythium ultimum*.

EXAMPLE VII

For determination of foliar fungicidal activity for the herein disclosed compounds, the following screen was used. The candidate compound is applied at 200 ppm to Bonny Best variety of tomato plants which have 2–4 true leaves. The treated plants are held at a relative humidity of 100% for 48 hours allowing ideal conditions for fungal invasion to occur. The plants are removed to the greenhouse bench and held for 7–10 days after which visual ratings are made. Ratings are by Infection Index (II) where 0 = no infection or 100% control, and 10 = 100% infection or no control.

To inoculate the plants, a spore suspension of early blight fungus (*Alternaria solani*) is prepared and sprayed on the plant until it reaches the point of runoff.

EXAMPLE VIII

For determination of acaricidal activity for the herein disclosed compounds, the following screening procedure was used: To evaluate a compound as a contact acaricide, the solution is sprayed at 15 psi onto the leaves of bean seedlings infested with mites as a 0.1% concentration. The sprayed plants are inoculated 24 hours later. In the case of systemic testing, the chemical is added to the nutrient solution in which the bean seedling is growing at a concentration of 20 ppm. After three days, mites are added to the leaves grown in the treated solution. In both cases, five days later counts are made and percent kill determined.

Two spotted spider mites (*Tetranychus urticae*) are used in these tests and pinto beans (*Phaseolus vulgaris*) in the cotylendonary stage is the host plant species used.

EXAMPLE IX

For determination of nematocidal activity for the herein disclosed compounds, the following acreening procedure was used: The roots of established tomato plants, grown in the presence of root knot (*Meloidogyne incognita*) nematodes and with adequately galled roots, are cut into small segments. The root segments are added to sterile soil and thoroughly mixed. The root knot infested soil is allowed to set for three days. During this period many larva will emerge from the decaying plant roots yielding a high potential of root knot inoculum soil. A quantity of the soil mixture is added to 8 oz. cups. Finally, 10 mls of the candidate nematocide at 20 ppm is added to the infested soil and thoroughly blended. The treated soil is removed from the jar and placed in an 8 oz. cup. The treated soil is allowed to aerate for 48 hours. Finally, cucumber seeds are planted in the treated soil. After 3-4 weeks, evaluations are made based on the galls occurring on the developing cucumber seedlings. The system used is the Root-Knot Index (RKI) based on a 0-10 rating where 0 = No galls and 10 = 100% galling.

EXAMPLE X

For determination of insecticidal activity for the herein disclosed compounds, the following screening procedure was used:

A. Screwworm Test

The candidate compound was evaluated as an insecticide on screwworms at rates of 0.3125-10.0%. The solutions were applied on 1st, 2nd, and 3rd instar larvi and on eggs.

Two reps of each larvi instar and the eggs were placed on black filter paper in petri dishes and sprayed with 5 ml total volume at each concentration. Ratings were made 48 hours following application.

B. White Fly Test

White fly infested tobacco (Nicotiana) plants were sprayed with a 1% solution of candidate test compound. Within 12 hours after application of the chemical, all white flies were either dead or had left the tobacco plants. White fly populations were too large to make quantitative counts, so visual observations were made.

C. Pea Aphid Test

The candidate compounds were appleid in a 0.5% solution to pea aphids and pea seedling plants in a contact test using a Waters vertical spray tower. The spray descends through an 8 inch stainless steel cylinder to the test insects and plants 44 inches below the atomizer. The spray tower is operated at 10 p.s.i. and discharges about 30 milliliters of spray per minute through a Devilbiss atomizer. The insects and seedlings were sprayed for a 15 second period and held for forty-eight hour mortality determinations.

D. Southern Armyworm Test

Excised lima bean leaves were dipped into 0.05% solutions of the candidate compounds and when dry were offered to 10 larvae of the Southern armyworm (late third instar) for a 48 hour feeding period.

EXAMPLE XI

The following compounds exhibited herbicidal, fungicidal, acaricidal, nematocidal and insecticidal properties:

4-nitro-1,2,3-benzotrisulfide
4-nitro-6-trifluoromethyl-1,2,3-benzotrisulfide
4-nitro-6-chloro-1,2,3-benzotrisulfide
4-dimethylamino-5-nitro-6-trifluoromethyl-1,2,3-benzotrisulfide
4-nitro-6-trifluoromethyl-1,2,3-benzotrisulfoxide (2).

It should be understood by those skilled in the art that various modifications may be made in the present invention without departing from the spirit and scope thereof as described in the specification and defined in the appended claims.

What is claimed is:

1. A compound selected from the group consisting of those of the formulae:

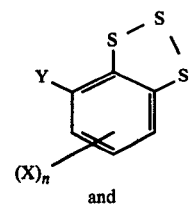

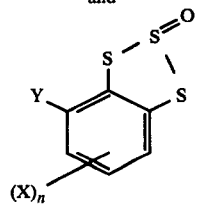

wherein Y is selected from nitro and trifluoromethyl; X is selected from alkyl and alkenyl of up to 6 carbon atoms, nitro, trichloromethyl, trifluoromethyl, trifluoromethoxy, trifluoromethylthio, trifluoromethylsulfoxyl, trifluoromethylsulfonyl, methoxymethyl, cyano, carboxy, carbamyl, halogen (F, Cl, Br, I), hydroxy, acetylamino, amino, N-phenylamino, N,N-diallylamino, alkoxy, dimethylaminodithiocarbamyl, carboalkoxy, alkylthio, mono- and dialkylamino, N-alkylcarbamyl, N,N-dialkylcarbamyl, alkylsulfoxy, alkylsulfonyl, said alkyl groups containing from 1 to 4 carbon atoms; n is an integer from 0 to 3; and salts thereof.

2. A compound as claimed in claim 1 having formula I wherein Y is nitro and n is zero which is 4-nitro-1,2,3-benzotrisulfide.

3. A compound as claimed in claim 1 having formula I wherein Y is nitro and n is 1.

4. The compound as claimed in claim 3 which is 4-nitro-6-trifluoromethyl-1,2,3-benzotrisulfide.

5. The compound as claimed in claim 3 which is 4-nitro-6-chloro-1,2,3-benzotrisulfide.

6. A compound as claimed in claim 1 having formula I wherein Y is trifluoromethyl and n is 2.

7. The compound as claimed in claim 6 which is 7-dimethylamino-6-nitro-4-trifluoromethyl-1,2,3-benzotrisulfide.

8. A compound as claimed in claim 1 having formula II wherein Y is nitro and n is one.

9. The compound as claimed in claim 8 which is 4-nitro-6-trifluoromethyl-1,2,3-benzotrisulfoxide (2).

10. A process for preparing compounds of the formula:

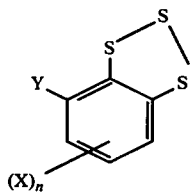

wherein Y is selected from hydrogen, cyano, alkylsulfonyl, nitro and trifluoromethyl; X is selected from alkyl and alkenyl of up to 6 carbon atoms, nitro, trichloromethyl, trifluoromethyl, trifluoromethoxy, trifluoromethylthio, trifluoromethylsulfoxyl, trifluoromethylsulfonyl, methoxymethyl, cyano, carboxy, carbamyl, halogen (F, Cl, Br, I), hydroxy, acetylamino, amino, N-phenylamino, N,N-diallylamino, alkoxy, dimethylaminodithiocarbamyl, carboalkoxy, alkylthio, mono- and dialkylamino, N-alkylcarbamyl, N,N-dialkylcarbamyl, alkylsulfoxy, alkylsulfonyl, said alkyl groups containing from 1 to 4 carbon atoms; n is an integer from 0 to 3; and salts thereof which comprises reacting a 1,3-benzodithiole-2-one of the formula:

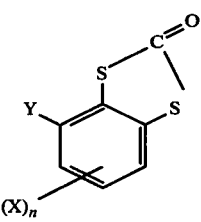

wherein Y, X and n are as defined above with a sulfurizing agent and recovering product.

11. The process of claim 10 wherein said reaction is carried out in the presence of a solvent.

12. The process of claim 10 wherein said sulfurizing agent is selected from sodium trithiocarbonate, sodium hydrosulfide and potassium thiocyanate.

13. The process of claim 10 for preparing compounds wherein Y is nitro and n is zero which is 4-nitro-1,2,3-benzotrisulfide which comprises reacting 4-nitro-1,3-benzodithiole-2-one with sodium hydrosulfide.

14. The process of claim 10 for preparing a compound wherein Y is nitro and n is 1 which comprises reacitng a 1,3-benzodithiole-2-one of formula III wherein Y is nitro and n is 1 with said sulfurizing agent and recovering product.

15. The process of claim 14 for preparing 4-nitro-6-trifluoromethyl-1,2,3-benzotrisulfide wherein 4-nitro-6-trifluoromethyl-1,3-benzodithiole-2-one is reacted with sodium hydrosulfide.

16. The process of claim 14 for preparing 4-nitro-6-chloro-1,2,3-benzotrisulfide wherein 4-nitro-6-chloro-1,3-benzodithiole-2-one is reacted with sodium hydrosulfide.

17. The process of claim 10 for preparing a compound wherein Y is trifluoromethyl and n is 2 which comprises reacting a 1,3-benzodithiole-2-one of formula III wherein Y is trifluoromethyl and n is 2 with said sulfurizing agent and recovering product.

18. The process of claim 17 for preparing 7-dimethylamino-6-nitro-4-trifluoromethyl-1,2,3-benzotrisulfide wherein 7-dimethylamino-6-nitro-6-trifluoromethyl-1,3-benzodithiole-2-one is reacted with sodium hydrosulfide.

19. A process for preparing compounds of claim 1 having the formula

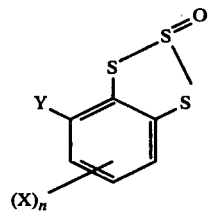

which comprises subjecting compounds having formula I wherein Y, X and n are as defined in claim 1 to peroxidation conditions and recovering product.

20. The process of claim 19 for preparing compounds of formula II wherein Y is nitro and n is 1.

21. The process of claim 20 for preparing the compound 4-nitro-6-trifluoromethyl-1,2,3-benzotrisulfoxide (2) which comprises subjecting the compound 4-nitro-6-trifluoromethyl, 1,2,3-benzotrisulfide-2-one to peracetic acid conditions.

22. A method of treating pests associated with growing plants to beneficially enhance the growth and/or yield-potential of said growing plants which comprises treating soil, seed or said plants with a biocidally active amount of a compound selected from the group consisting of those of the formulae:

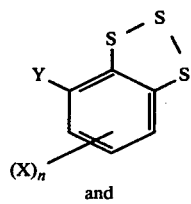

and

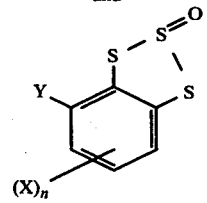

wherein Y is selected from hydrogen, cyano, alkylsulfonyl, nitro and trifluoromethyl; X is selected from alkyl and alkenyl of up to 6 carbon atoms, nitro, trichloromethyl, trifluoromethyl, trifluoromethoxy, trifluoromethylthio, trifluoromethylsulfoxyl, trifluoromethylsulfonyl, methoxymethyl, cyano, carboxy, carbamyl, halogen (F, Cl, Br, I), hydroxy, acetylamino, amino, N-phenylamino, N,N-diallylamino, alkoxy, dimethylaminodithiocarbamyl, carboalkoxy, alkylthio, mono- and dialkylamino, N-alkylcarbamyl, N,N-dialkylcarbamyl, alkylsulfoxy, alkylsulfonyl, said alkyl groups containing from 1 to 4 carbon atoms; n is an integer from 0 to 3; and salts thereof.

23. The method as claimed in claim 22 wherein said compound has formula I wherein Y is nitro and n is zero which is 4-nitro-1,2,3-benzotrisulfide.

24. The method as claimed in claim 22 wherein said compound has formula I wherein Y is nitro and n is 1.

25. The method of claim 24 wherein said compound is 4-nitro-6-trifluoromethyl-1,2,3-benzotrisulfide.

26. The method of claim 24 wherein said compound is 4-nitro-6-chloro-1,2,3-benzotrisulfide.

27. The method of claim 22 wherein said compound has formula I wherein Y is trifluoromethyl and n is 2.

28. The method of claim 27 wherein said compound is 7-dimethylamino-6-nitro-4-trifluoromethyl-1,2,3-benzotrisulfide.

29. The method of claim 22 wherein said compound has formula II wherein Y is nitro and n is 1.

30. The method of claim 29 wherein said compound is 4-nitro-6-trifluoromethyl-1,2,3-benzotrisulfoxide (2).

* * * * *